(12) United States Patent
Dunn et al.

(10) Patent No.: US 10,580,078 B2
(45) Date of Patent: Mar. 3, 2020

(54) SYSTEM AND METHOD FOR ASSESSING HEALTHCARE RISKS

(71) Applicant: OptumInsight, Inc., Eden Prairie, MN (US)

(72) Inventors: Daniel L. Dunn, Bedford, MA (US); Dogu Celebi, Acton, MA (US)

(73) Assignee: OptumInsight, Inc., Eden Prairie, MN (US)

( * ) Notice: Subject to any disclaimer, the term of this patent is extended or adjusted under 35 U.S.C. 154(b) by 469 days.

(21) Appl. No.: 14/709,895

(22) Filed: May 12, 2015

(65) Prior Publication Data
US 2015/0339778 A1 Nov. 26, 2015

Related U.S. Application Data

(63) Continuation of application No. 10/688,858, filed on Oct. 17, 2003, now Pat. No. 9,058,629.

(51) Int. Cl.
*G16H 50/30* (2018.01)
*G06Q 40/08* (2012.01)
*G06Q 50/22* (2018.01)

(52) U.S. Cl.
CPC .............. *G06Q 40/08* (2013.01); *G06Q 50/22* (2013.01)

(58) Field of Classification Search
CPC ................................ G06Q 40/08; G16H 50/30
See application file for complete search history.

(56) References Cited

U.S. PATENT DOCUMENTS

| | | | |
|---|---|---|---|
| 5,486,999 A | 1/1996 | Mebane |
| 5,498,524 A | 3/1996 | Hall |
| 5,544,044 A | 8/1996 | Leatherman |
| 5,557,514 A | 9/1996 | Seare et al. |
| 5,706,441 A | 1/1998 | Lockwood |
| 5,715,451 A | 2/1998 | Marlin |
| 5,752,236 A | 5/1998 | Sexton et al. |
| 5,819,228 A | 10/1998 | Spiro |
| 5,835,897 A | 11/1998 | Dang |
| 5,845,254 A | 12/1998 | Lockwood et al. |
| 5,924,073 A | 7/1999 | Tyuluman et al. |
| 5,940,802 A | 8/1999 | Hildebrand |
| 5,956,689 A | 9/1999 | Everhart, III |
| 5,970,463 A | 10/1999 | Cave et al. |
| 5,976,082 A | 11/1999 | Wong et al. |
| 6,000,828 A | 12/1999 | Leet |
| 6,061,657 A | 5/2000 | Whiting-O'Keefe |

(Continued)

FOREIGN PATENT DOCUMENTS

WO  WO 99/44167  9/1999

OTHER PUBLICATIONS

"Using Prescription Drug Data for Risk Adjustment and Underwriting/Rating"; Society of Actuaries; 2002.*

(Continued)

*Primary Examiner* — John A Pauls
(74) *Attorney, Agent, or Firm* — Dorsey & Whitney LLP

(57) ABSTRACT

A system and method for receiving demographic data on a patient and data on at least one pharmacy service prescribed for the patient; assigning a unique drug class to each pharmacy service; using the unique drug classes for ordering the pharmacy services according to a predetermined hierarchy of classes; and providing a risk score for the patient using the ordered pharmacy services.

18 Claims, 6 Drawing Sheets

(56) References Cited

U.S. PATENT DOCUMENTS

| | | | |
|---|---|---|---|
| 6,163,770 | A | 12/2000 | Gamble et al. |
| 6,223,164 | B1 | 4/2001 | Sear et al. |
| 6,266,645 | B1 | 7/2001 | Simpson |
| 6,363,393 | B1 | 3/2002 | Ribitzky |
| 6,370,511 | B1 | 4/2002 | Dang |
| 6,385,589 | B1 | 5/2002 | Trusheim et al. |
| 6,456,979 | B1 | 9/2002 | Flagg |
| 6,484,144 | B2 | 11/2002 | Martin et al. |
| 6,578,003 | B1 | 6/2003 | Camarda et al. |
| 6,581,204 | B2 | 6/2003 | DeBusk et al. |
| 6,587,829 | B1 | 7/2003 | Camarda |
| 6,629,095 | B1 | 9/2003 | Wagstaff et al. |
| 6,802,810 | B2 | 10/2004 | Ciarniello et al. |
| 2001/0020229 | A1 | 9/2001 | Lash |
| 2001/0029322 | A1 | 10/2001 | Iliff |
| 2002/0188476 | A1 | 12/2002 | Bienvenu et al. |
| 2003/0167189 | A1 | 9/2003 | Lutgen et al. |
| 2003/0195772 | A1 | 10/2003 | Meek et al. |
| 2004/0024620 | A1 | 2/2004 | Robertson et al. |
| 2004/0049408 | A1 | 3/2004 | Voss et al. |

OTHER PUBLICATIONS

Risk adjusted premium subsidies and risk sharing: key elements of the competetive sickness fund market in the Netherlands; Lamers et al.; Health Policy 65; 2003.*

Health-based risk adjustment: Improving the pharmacy-based cost group model to reduce gaming possibilities; Lamers et al.; Eur J Health Econom; 2003.*

Implementation of Risk Adjustment for Medicare; Ingber; Health care Financing Review; 2000.*

"Pharmacy Cost Groups"; Lamers; Medical care; vol. 37, No. 8, pp. 824-830 (Year: 1999).*

Alexandre, Leslie M."High Cost Patients in a Free-For-Service Medical Plan, The Case for Earlier Intervention", *Medical Care*, Feb. 1990, vol. 28, No. 2, pp. 112-123.

Clark, Daniel O. et al., "A Chronic Disease Score with Empirically Derived Weights", *Medical Care*, 1995, vol. 33, No. 8, pp. 783-795.

Roblin, Douglas W ., et al., "A Low-Cost Approach to Prospective Identification of Impending High-Cost Outcomes", *Medical Care*, vol. 37, No. 11 pp. 1155-1163.

Steen, Paul, M., "Approaches to Predictive Modeling, "*Ann Thorac Surg* 1994:58:1836-40.

Imagine If You Could Obtain Accurate Clinical Data From the Point of Care. MD Trends Web Site. Dec. 4, 2000. (Retrieved on Nov. 3, 2002). Retrieved from the internet:< URL: http://web.archive.org/web/20001204191600/www.mdtrends.com/>.

"Looking to manage care more closely. (new technique in case management to manage chronic illness and high-risk pregnancies)", Shoor, Rita, Business & Health, v11, n10, p. 46 (6), Sep. 1993, Dialog File 149, Acc. No. 01429566.

The burden of Illness in Canada, accessed at www.burdenofilness.ca Dec. 3, 2003.

Ingenix Announces New Clinical Care Groups' Episode Grouping Tool Pharmaceutical Data. Apr. 11, 2000. Ingenix, Inc. [Retrieved from the Internet on Oct. 21, 2002]. URL: http://www.ingenix.com/releases/4-11-00.html Ingenix Products and Services. May 11, 2000. Ingenix, Inc. [Retrieved from the Internet on Aug. 20, 2003]. URL:<http://web.archive.org/web/20000511154002/www.ingenix.eom/products/products.html>.

* cited by examiner

Table 1
Pharmacy Risk Groups

| PRG | Description |
|---|---|
| 01 | Anti-Infectives |
| 01.01 | Amebicides and Antifungal Antibiotics |
| 01.02 | Aminoglycosides excluding Cystic Fibrosis Agents |
| 01.03 | Arthritis Agents |
| 01.04 | Antituberculosis Agents |
| 01.05 | Cephalosporins, Macrolides, other Selected Anti-Infective Agents |
| 01.06 | HIV Antiviral Agents |
| 01.07 | Leprostatics |
| 01.08 | Miscellaneous Antibiotics, NEC |
| 01.09 | Non-HIV Antiviral Agents, NEC |
| 01.10 | Quinolones |
| 01.11 | Higher Cost Anti-Infectives, NEC |
| 01.81* | Multiple Selected Anti-Infective Agents, I |
| 01.82* | Multiple Selected Anti-Infective Agents, II |
| 02 | Antineoplastics |
| 02.01 | Antineoplastics, I (Nitrogen Mustards, Nitrosureas, Anthracycline Antibiotics) |
| 02.02 | Antineoplastics, II (Androgens/Anti-Androgens for Chemotherapeutic Use) |
| 02.03 | Antineoplastics, III (Antimetabolites and Selected Chemotherapy Agents) |
| 02.04 | Antineoplastics, IV (Gonadotropin-Releasing Hormones for Chemotherapy) |
| 02.05 | Antineoplastics, V (Miscellaneous Antineoplastics, NEC) |
| 02.06 | Antineoplastics, VI (Hepatitis Agents) |
| 02.07 | Antineoplastics, VII (Agents used to treat Breast Cancer, I) |
| 02.08 | Antineoplastics, VIII (Agents used to treat Breast Cancer, II) |
| 03 | Blood Formation and Modification |
| 03.01 | Antihemophilic Agents |
| 03.02 | Anticoagulants - Antiplatelets, Coumarin, Heparins, Glycosaminoglycans |
| 03.03 | Folic Acid-Folinic Acid Products |
| 03.04 | Hematopoietic Agents |
| 03.05 | Iron and Iron Combinations |
| 03.06 | Hemostatics and Thrombolytic Enzymes |
| 03.07 | Vitamin B12 and K Products |

| PRG | Description |
|---|---|
| 04 | Cardiovascular (CV) |
| 04.01 | Beta Adrenergic Antagonists, Alpha 1-Adrenergic Antagonists |
| 04.02 | Carvedilol, Nitrates and Nitrites, Digoxin |
| 04.03 | Antihypertensive Agents |
| 04.04 | Antiarrhythmic Agents |
| 04.05 | Other Cardiovascular Agents, NEC |
| 04.06 | Calcium Channel Antagonists |
| 04.07 | Vasodilating Agents |
| 04.08 | Vasopressors used in Shock, Midadrine HCL |
| 04.81* | Higher Risk CAD, Anti-Infectives/Antibiotics Comorbidity |
| 04.82* | Higher Risk CAD, CNS Comorbidity |
| 04.83* | Higher Risk CAD, GI Comorbidity |
| 04.84* | Higher Risk CAD, Insulin Comorbidity |
| 04.85* | Higher Risk CAD, Respiratory Comorbidity |
| 04.86* | Mod/Lower Risk CAD/Hypertension, GI Comorbidity |
| 04.87* | Mod/Lower Risk CAD/Hypertension, Insulin Comorbidity |
| 04.88* | Mod/Lower Risk CAD/Hypertension, Respiratory Comorbidity |
| 04.89* | Loop and Higher Risk Diuretics Comorbidity |
| 04.90* | Higher Risk CAD, 3 or more Comorbids |
| 05 | Central Nervous System (CNS) |
| 05.01 | Migraine Agents and Selected Salicylates |
| 05.02 | Agents used to treat Alzheimer's Disease |
| 05.03 | Agents used to treat Multiple Sclerosis |
| 05.04 | Agents used to treat ALS |
| 05.05 | Agents used to treat Parkinson Disease |
| 05.06 | Amphetamines and Miscellaneous CNS Stimulants, NEC |
| 05.07 | Anorexiants |
| 05.08 | Antiemetic Agents used in treatment of Cancer |
| 05.09* | Antiemetic Agents, NEC, >18 years of age |
| 05.10 | Antipsychotic and Antimanic Agents |
| 05.11 | Antivertigo Agents Anticholinergics |

FIG. 3a

Table 1 (continued)
Pharmacy Risk Groups

| PRG | Description |
|---|---|
| 05 | Central Nervous System (CNS), Continued |
| 05.12 | Barbiturate General Anesthetics and Sedative Hypnotics |
| 05.13 | Antidepressants, Antianxiety Agents, Nonbarbiturate Sedative Hypnotics, NEC |
| 05.14 | Narcotic Agonist Analgesics and Agonist-Antagonist Combinations |
| 05.15 | Centrally Acting Analgesics, Muscle Relaxants and Narcotic Analgesic |
| 05.16 | Other CNS Agents, NEC |
| 05.17 | Anticonvulsants |
| 05.18 | Selected Skeletal Muscle Relaxants, used in treatment of Multiple Sclerosis |
| 05.19 | Narcotic Agonist Analgesics, Higher Risk |
| 05.81* | Antipsychotic/Anti-Manic with Antidepression/Antianxiety Agents |
| 05.82* | Higher Risk Narcotic Agonist Analgesics with other Analgesic Agents |
| 05.83* | Selected CNS Agents, Single, with Antidepression/Antianxiety |
| 05.84* | Selected CNS Agents, Multiple, with Antidepression/Antianxiety |
| 05.85* | Antiemetics used in treatment of Cancer, w evidence of Antineoplastics |
| 07 | Electrolyte/Caloric/Water Balance |
| 07.01 | Acidifying Agents, Alkenalyzing Agents |
| 07.02 | Agents used to treat Electrolyte Disorders, Ion Exchange Resins |
| 07.03 | Ammonia Detoxicants |
| 07.04 | Carbonic Anhydrase Inhibitors |
| 07.05 | Diuretics and Thiazides, excl Loop and Higher Risk Diuretics, > 18 yrs of age |
| 07.06 | Diuretics and Thiazides, excl Loop and Higher Risk Diuretics, 0-18 yrs of age |
| 07.07 | Loop Diuretics |
| 07.08 | Higher Risk Diuretics |
| 08 | Gastrointestinal Agents (GI) |
| 08.01 | Agents used to treat Inflammatory Bowel Disease |
| 08.02 | Antidiarrheal/Antiflatulent Agents |
| 08.03 | Antacids, Anticholinergics and other Selected GI Agents, NEC, > 18 yrs of age |
| 08.04 | Gastrointestinal Prokinetic Agents |
| 08.05 | GI Agents, NEC |
| 08.06 | Proton Pump Inhibitors |
| 08.81* | Selected GI Agents with 0-18 years of age |

| PRG | Description |
|---|---|
| 09 | Hormones and Synthetic Agents |
| 09.01 | Antidiabetic Agents, excluding Insulin |
| 09.02 | Antithyroid Agents and Thyroid Hormones |
| 09.03 | Bone Resorption Inhibitors, Agents associated w treatment of Osteoporosis |
| 09.04 | Estrogens, Progestins, Oxytocics |
| 09.05* | Glucocorticoids, > 18 years of age |
| 09.06* | Glucocorticoids, 0-18 years of age |
| 09.07 | Growth Hormones |
| 09.08 | Ovulation Stimulants |
| 09.09 | Anabolic Steroids |
| 09.10 | Insulin |
| 09.11 | Vasopressin Derivatives and other selected Hormones/Synthetic Substitutes |
| 09.12 | Natural and Synthetic Androgens |
| 09.81* | Insulin, Anti-Infectives/Antibiotics Comorbidity |
| 09.82* | Insulin, CNS Agents Comorbidity |
| 09.83* | Insulin, Gastrointestinal Agents Comorbidity |
| 09.84* | Non-Insulin Diabetes, Anti-Infectives/Antibiotics Comorbidity |
| 09.85* | Non-Insulin Diabetes, CNS Agents Comorbidity |
| 09.86* | Insulin, 3 or more Comorbidities |
| 09.87* | Non-Insulin Diabetes, 3 or more Comorbidities |
| 10 | Nutritional Agents |
| 10.01 | B Vitamins and Derivatives |
| 10.02 | Calcium Supplements-Oral |
| 10.03 | Prenatal – Vitamins / Minerals / Combination Products |
| 10.04 | Nutritional Supplements for Deficiency States and Vitamin D Analogs |

FIG. 3b

Table 1 (continued)
Pharmacy Risk Groups

| PRG | Description | | PRG | Description |
|---|---|---|---|---|
| 11 | R spiratory | | | Other Agents |
| 11.01 | Inhaled Corticosteroids | | 12.01 | Higher Cost Immunologic Agents |
| 11.02 | Antihistamines | | 12.02 | Agents for Xerostomia |
| 11.03 | Leukotriene Receptor Antagonists | | 15.01 | Oral Antifungals |
| 11.04 | Xanthine-Sympathomimetics and other selected Respiratory Agents | | 17.01 | Agents to Treat Impotence |
| 11.05 | Xanthine Derivatives | | 17.02 | Cholinergic Muscle Stimulants |
| 11.06 | Inhaled Anticholinergic Agents | | 17.03 | Urinary Anticholinergics |
| 11.81* | Inhaled Anticholinergic Agents with other Respiratory Agents | | 17.04 | Narcotic Antagonist Antidotes |
| 11.82* | Respiratory, 3 Comorbidities | | 17.05 | Chelating Antidotes - Penicillamin, Trientine |
| 13 | Topical Opthalmic Preparations | | 17.06 | Agents to Treat Enzyme Deficiency States |
| 13.01 | Opthalmic Antihistamines, Anti-Allergy and Non-Steroidal Anti-Inflammatories | | 30.01 | Agents to Treat Cystic Fibrosis, I |
| 13.02 | Agents to Treat Glaucoma | | 30.02 | Agents to Treat Cystic Fibrosis, II |
| 13.03 | Cycloplegic Mydriatics | | | |
| 13.04 | Opthalmic Anti-infectives and Corticosteroids | | | |
| 16 | Topical Skin and Mucous Membranes | | | |
| 16.01 | Miscellaneous Topical Skin and Mucous Membrane Agents | | | |
| 16.02 | Topical Corticosteroids | | | |
| 16.03 | Topical Enzymes and Combinations | | | |
| 16.04 | Topical Skin and Mucus Membrane Anesthetics | | | |
| 16.05 | Topical Wound Healing Agents | | | |

Note: An asterisk (*) indicates an added PRG or an initial PRG modified by additional logic.

FIG. 3c

Table 2
Examples of PRG Risk Score Assignment

Example 1
Male, Age 58

| DCC | Description | PRG | Description | Risk Weight |
|---|---|---|---|---|
| 01500 | Ciprofloxacin HCL / Lactate IV | 01.10 | Quinolones | 0.3495 |
| 25605 | Lisinopril | 04.03 | Antihypertensive Agents | 0.2819 |
| 00600 | Erythromicin | 01.05 | Cephalosporins, Macrolides, and other Selected Anti-Infective Agents | 0.0925 |
| 32000 | Fluoxetine HCL | 05.13 | Antidepressants, Antianxiety Agents and Nonbarbituate Sedative Hypnotics, NEC | 0.4729 |
| 32001 | Sertraline | 05.13 | Antidepressants, Antianxiety Agents and Nonbarbituate Sedative Hypnotics, NEC | 0.0000 |
| 30302 | Ibuprofen | ----- | Not assigned to a PRG | 0.0000 |
| Age-Sex | | Age-Sex Group | | |
| | Male, 58 | | Males, 55 to 64 | 1.0219 |
| | | | Total Risk Score | 2.2187 |

Example 2
Male, Age 58

| DCC | Description | PRG | Description | Risk Weight |
|---|---|---|---|---|
| 58201 | Flunisolide | 11.02 | Antihistamines | 0.1195 |
| 24901 | Carvedilol | 04.02 | Carvedilol, Nitrates and Nitrites, Digoxin | 0.3131 |
| 50401 | Insulin | 09.10 | Insulin | 1.0682 |
| | Co-morbid PRG | 04.84 | Higher Risk CAD, Insulin Comorbidity | 1.2376 |
| Age-Sex | | Age-Sex Group | | |
| | Male, 58 | | Males, 55 to 64 | 1.0219 |
| | | | Total Risk Score | 3.7602 |

Example 3
Female, Age 52

| DCC | Description | PRG | Description | Risk Weight |
|---|---|---|---|---|
| 34604 | Riluzole | 05.04 | Agents to treat ALS | 12.0071 |
| 32000 | Fluoxetine HCL | 05.13 | Antidepressants, Antianxiety Agents and Nonbarbituate Sedative Hypnotics, NEC | 0.4729 |
| Age-Sex | | Age-Sex Group | | |
| | Female, 52 | | Females, 45 to 54 | 0.6650 |
| | | | Total Risk Score | 13.1450 |

FIG. 4

SYSTEM AND METHOD FOR ASSESSING HEALTHCARE RISKS

CROSS-REFERENCE TO RELATED APPLICATIONS

This application is a continuation of U.S. application Ser. No. 10/688,858 filed on Oct. 17, 2003, the contents of which are herein incorporated by reference in its entirety.

FIELD OF THE INVENTION

The invention disclosed broadly relates to the field of methods for assessing risk and more particularly relates to the field of assessing the risks for issuing healthcare insurance.

BACKGROUND OF THE INVENTION

Assessing member health risk has become a critical need of healthcare organizations. An individual's health risk or "illness burden" is a measure of the relative resources expected to be required for their medical care. It can vary for a number of reasons, including a person's current health, genetic make-up, socio-economic status, and environment. Whether to support accurate payment rates, meaningful comparisons of provider performance, or the identification of patients of highest risk, sound methods of health risk assessment are an important tool for any health care organization.

Adjusting for differences in health risk can be thought of as a two-step process. The first step, risk assessment, involves the measurement of the expected health care costs or utilization of an individual or groups of individuals. Risk adjustment is the mechanism for adjusting for differences in risk, as measured by the risk assessment. In all applications, risk adjustment will only be as good as the underlying risk assessment method. There is a need for a new approach to health risk assessment.

SUMMARY OF THE INVENTION

A method for assessing risk of insuring a healthcare patient, the method comprises steps of: receiving demographic data on a patient and data on at least one pharmacy service prescribed for the patient; assigning a unique drug class to each pharmacy service; using the unique drug classes for ordering the pharmacy services according to a predetermined hierarchy of classes; and providing a risk score for the patient using the ordered pharmacy services.

BRIEF DESCRIPTION OF THE DRAWINGS

FIGS. 3a-c show a first table listing pharmacy risk groups.

FIG. 4 shows a second table illustrating examples of PRG Risk Score Assignment.

DETAILED DESCRIPTION

Figure 1:
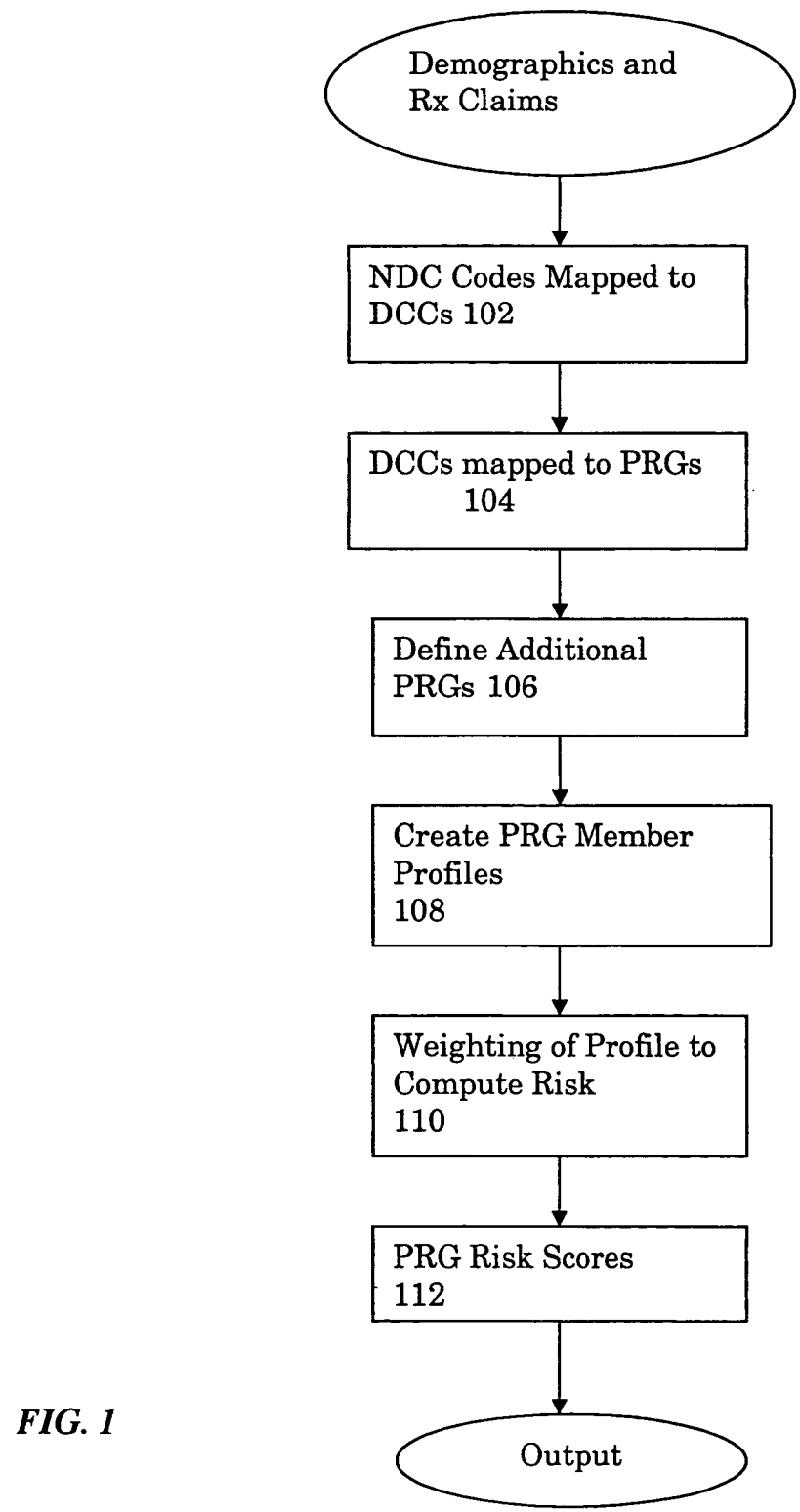
FIG. 1 is a block diagram providing an overview of a process according to an embodiment of the invention.

Referring to FIG. 1, there is shown a block diagram providing an overview of a process according to an embodiment of the invention. The method can be implemented as software executed by any suitable information processing system. The method discussed herein uses a set of risk groups (identified by the trademark "PRG") to provide a solution to overcome the detriments of present systems. PRGs use a patient's pharmaceutical prescriptions and demographic information to assess their prospective health risk. PRGs are designed to assist organizations that do not have access to medical claims or desire to perform more timely health risk assessment. Although medical claims can provide advantages in measuring patient risk there is a need for a method for assessing risks in health care that avoids the detriments of claims-based assessment. In particular, the fundamental building blocks of PRGs are a patient's mix of pharmacy prescriptions—the unique occurrences of a drug used in treating a disease or condition and how that agent relates to others prescribed for the patient. The nature and mix of these treatments provides a pharmacy-based clinical profile for a patient that can serve as a marker of his/her future need for medical care. The method comprises the following elements:

1. Drug Code Hierarchy—Using the NDC codes recorded on pharmacy claims and a hierarchy developed by Symmetry Health Data Systems, each pharmacy service for a member is first assigned to a unique drug class called a DCC;
2. DCCs to PRGs—DCCs for a member are further categorized into one of 120 initial pharmacy risk groups (PROs). The PRGs are markers of member risk and combine DCCs of similar clinical and risk characteristics;
3. Additional PRGs—further PRGs are defined based on patient age and the combination of initial PROs observed. These PRGs reflect co-morbidities or other characteristics that suggest a patient is of higher risk.
4. PRG Profile—Age, gender and mix of PRGs provide a clinical and demographic risk profile for a member. Members can be assigned zero, one, or more PRGs. Members with pharmacy treatments that indicate multiple medical conditions will have multiple PRGs;
5. PRG Risk Score—Using pre-determined weights and a member's PRG profile, a risk score is computed. A member's risk score is simply the sum of the weights attached to each PRG and demographic characteristic observed in their profile.

Symmetry's Drug Code Hierarchy—Mapping NDCs to DCCs. The National Drug Codes (NDCs) on a member's pharmacy claims provide a detailed description of their particular agents prescribed, including the labeler (manufacturer, packager, or distributor), the product itself (with strength, dosage and formulation), and how the drug is packaged. The details included in an NDC code are useful in many applications. However, the key information for health risk assessment comprises the general description of the agent itself, a description that can be linked to a therapeutic usage—the types of diseases and conditions for which it is typically prescribed. If a strong link can be established between an agent and therapeutic usage, the drugs prescribed for a member can serve as a useful proxy for that member's overall morbidity and health risk.

A number of unique NDC codes are currently available to describe prescription drugs—too many groupings to support any practical approach to risk assessment. To categorize these codes, our method uses a robust, clinically-based classification system called the Drug Code Hierarchy. This system was initially developed by Symmetry Health Data Systems to support its Episode Treatment Group (ETG) methodology. Based on a series of clinical and statistical algorithms, ETGs combine inpatient and outpatient medical and pharmacy services into mutually exclusive and exhaustive categories called episodes of care. Examples of ETGs are insulin-dependent diabetes, with co-morbidity; congestive heart failure without co-morbidity; and ischemic heart disease, without AMI. Given its ability to categorize drugs for assignment to disease and condition episodes of care, the Drug Code Hierarchy provides a natural link between NDC code and therapeutic usage, a link that provides a sound basis for the development of a health risk assessment model.

Figure 2:
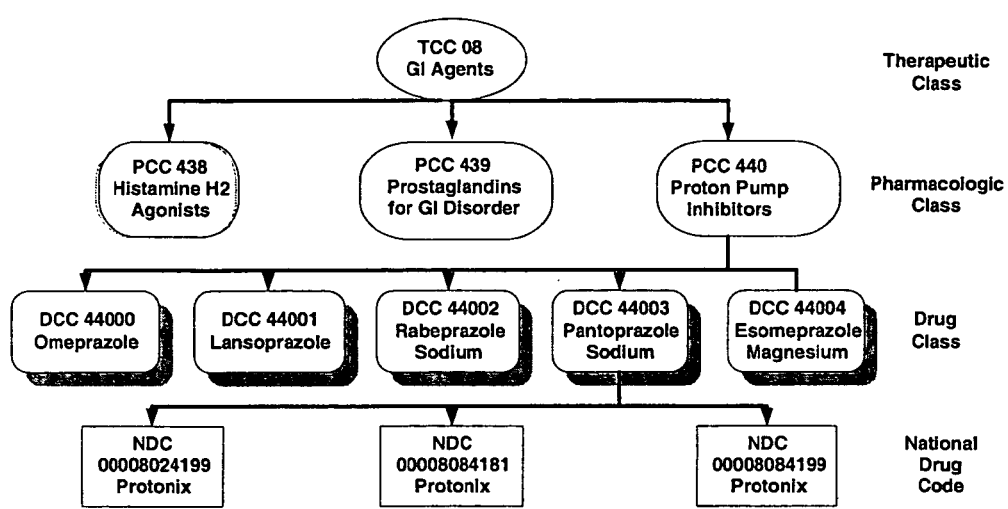
FIG. 2 shows a drug code hierarchy for use in a method according to the invention.

FIG. 2 provides an example of the different levels of classification provided by the Drug Code Hierarchy. The lowest level is the NDC code. NDC codes map uniquely into Drug Class Codes (DCCs) that describe the general ingredient for the NDC. DCCs are further assigned to Pharmacologic Class (PCCs) and Therapeutic Class (TCCs). The PCCs and TCCs provide the link between the general ingredient described by an NDC code and the typical therapeutic use. In this example—for GI Agents—the three NDC codes for Protonix all map to DCC 44003 (Pantaprazole Sodium). That DCC and other selected agents map to PCC 440 (Proton Pump Inhibitors) which further are assigned to the GI Agents TCC.

Referring again to FIG. 1, in step 102, the method uses the Drug Code Hierarchy and maps all NDC codes for a patient to a unique DCC. We assume a 12-month risk-marker period for a member. All available pharmacy claims for the previous 12-months for a member are used for mapping to DCCs and creating markers of risk.

Pharmacy Risk Groups (PRGs)—Mapping DCCs to PRGs.

Referring again to FIG. 1, in step 104 the DCCs are mapped to PRGs. The DCC grouping provides a record of the different drug ingredients identified for an individual. A key step in developing PRGs is deciding how these DCCs can best be used as markers of risk. One option is to use all of the approximately 3,000 DCCs as separate risk markers. This approach is not preferred for several reasons. First, such a large number of risk factors would likely produce relatively small sample sizes for some markers, resulting in implausible or imprecise estimates of their contribution to risk. Further, the level of clinical detail provided by the DCCs could also produce imprecision due to the potential overlap in the impact of clinically-related agents on patient risk—over or underestimating risk for members with different combinations of these agents.

We combine DCCs into larger groups to create PRGs. In mapping DCCs to PRGs the primary goal is combining drugs of similar clinical and risk characteristics. Both clinical input and empirical evidence guide this process. The mapping involves a number of steps and assumptions:

DCCs indicating the same disease or condition and patients of similar risk are combined. To enhance both clinical relevance and also homogeneity in terms of risk, the grouping of DCCs occurred primarily within the same PCC and TCC—with all agents in most PCCs assigned to the same PRG. Exceptions include agents typically used to treat clinically diverse patients, patients of differing risk, or both. In these cases, DCCs within the same PCC are assigned to separate PRGs;

DCCs with relatively low prevalence were combined with other DCCs based on clinical similarity and implications for risk assessment;

PRG assignment does not vary with the number of DCCs or prescriptions observed for an individual within the same PRG. Patients with single or multiple agents or prescriptions within a PRG receive identical assignments. Further, for practical and other reasons, measures of dosage recorded on pharmacy claims, such as days supply and metric quantity, also do not impact PRG assignment;

Not all DCCs are used. Many agents have no measurable impact on future risk for a patient and are not assigned to a PRG. Further, to promote consistency, pharmaceutical agents not typically covered and provided through a prescription drug benefit are not used. Agents administered largely in an inpatient or facility setting or distributed primarily over-the-counter are examples.

Using this approach, a total of 107 PRGs have been initially identified. These PRGs are described in Table 1 (shown in FIGS. 3a-c). Note that further PRGs can be defined for a patient based on the combinations of these initial PRGs and other criteria (in step 106).

Additional PRGs

Additional PRGs are defined based on observed combinations of the PRGs described in step 106. The majority of these added PRGs are designed to capture the impact on risk of a patient's co-morbidities. For example, a patient prescribed agents related to the treatment of coronary artery disease (CAD) who also has one or more prescriptions for insulin (suggesting diabetes) may have a different level of risk related to these agents than a patient with only the CAD agent or only insulin. A patient receiving multiple CAD-related agents from different PRGs is another example. For selected agents, separate PRGs were also defined depending on whether the age of the patient was 0-18 years or greater than 18, based on their differing impact on risk for children and adults. Glucocorticoid agents is one example. The final model includes 136 PRGs. The PRGs added or modified in Step 106 are noted in Table 1 with an asterisk (*).

PRG Profile

Next, in step 108, a member's age, gender and mix of PRGs are used to create his or her PRG profile. Seven age groups are used for each gender for this purpose—0-5, 6-11, 12-18, 19-34, 35-44, 45-54, and 55-64 years of age.

Every member is assigned to an age-sex group. Members can also be assigned to zero, one, or more PRGs depending on their mix of pharmacy agents. Members without pharmacy claims will have no PRGs. For these members, risk is based solely on age and gender.

Measuring the Contribution of PRGs to Member Risk—PRG Risk Weights.

The next step 110 is the assignment of a weight to each PRG and demographic marker of risk to provide a risk score 112. These weights describe the contribution to risk of being in a specific age-sex group or having a particular agent included in a PRG. The model of risk can be defined as:

$$Risk_i = \Sigma a_s * asex_{i,s} + \Sigma b_e * PRG_{i,p}$$

where Riski is the PRG risk score for person i; asexis and PRGi,p indicate their age-sex group (s); and PRG (p) assignments, and the a's and b's are the risk weights. The age-sex and PRG markers are a series of 0,1 variables, set to 1 if the marker is observed for an individual, 0 otherwise. Each member has their own profile of age-sex and PRGs. However, the risk weights are pre-defined and are the same for all individuals. The risk weights are pre-set and delivered as part of the PRG software. Alternatively, PRG customers with large patient populations (greater than 500,000 members) might want to estimate weights using their own experience. A person's risk score is the sum of these risk weights for each marker observed.

The risk weights for PRGs are estimated using multiple linear regression and enrollment and pharmacy claims data for a large managed care population. These data are also used to test the predictive accuracy of the PRG model, as described below. The PRG development data were obtained from the IHCIS National Managed Care Benchmarks Database.

Some applications of health risk assessment may require differing assumptions regarding the maximum dollar amount of interest for each member. To support this flexibility, PRG weights are estimated using different expenditure threshold assumptions. Expenditure threshold describes the level at which a higher-cost member's expenditures were truncated prior to deriving model weights. The application of a threshold amount has importance for several reasons. First, truncating expenditures for higher-cost members limits the impact of extreme outliers on model development and testing. Second, most applications of health risk assessment involve some use of a threshold or stop-loss. For example, when profiling the economic performance of primary care practitioners, some health plans will truncate expenditures for members with annual costs above some catastrophic amount, such as $25,000. Payment or rate setting often includes some allowance for higher cost members, either explicitly as part of the rate setting process, or through reinsurance by health plans.

Thresholds of $25,000, $50,000, $100,000 and $250,000 can be used for estimating model risk weights. Costs for members with annual expenditures exceeding these amounts are truncated to the particular threshold for that analysis—for example, a member with annual costs of $200,000 had their costs adjusted to $100,000 for the $100,000 threshold. PRG users can select one of these threshold options depending on their application.

Finally, health risk assessment typically focuses on projections of the relative health risk of total costs for a member, including all services. However, for some pharmacy-specific applications, users may desire an alternative outcome—member's health risk for pharmacy services only. To accommodate this, PRG users can select either total service costs (medical and pharmacy) or pharmacy costs alone as the outcome measured by the model. The same PRGs are used for each of these two outcomes and the different thresholds described above. However, the risk weights included in the model vary by both outcome and threshold selected.

Referring to FIG. 4, Table 2 provides examples of how PRG risk would be calculated for an individual—using the total cost outcome and a threshold assumption of $250,000.

As shown, for Example 1, over a 12-month period, a male, age 58 was observed to have six unique DCCs, that map to four different PRGs—quinolones; antihypertensive agents; selected antiinfectives (macrolides); and antidepressants/antianxiety. (Note that the second anti-depressant (DCC 32001) does not add additional risk. Further, the prescription for ibuprofen does not contribute to risk, since that DCC does not map to any PRG.) The individual's age and sex and these four PRGs describe their profile of risk. The sum of the weights assigned to these risk markers provides the overall risk scores for the individual—separate risk scores for the retrospective and prospective models.

The scores in Table 2 reflect each individual's measure of risk relative to that of the overall population used in developing PRGs. A score of 1.00 indicates risk comparable to that of the development population, a score of 1.10 indicates 10 percent greater risk, 0.85, 15 percent lower risk, and so on. The 58-year-old male described in Table 2, Example 1 has a PRG prospective risk score of 2.2187—indicating a level of future health risk more than two times that of the average for the large managed care population used in developing PRGs.

Example 2 shows a male, age 58 who prescription drugs translate into three unique DCCs, that map into three initial PRGs. These initial PRGs trigger a fourth PRO, based on the presence of both the carvedilol and insulin agents. This member receives separate risk weights for the carvedilol and the insulin PRGs and also receives a third weight due to the co-morbid PRG. Relative risk for this patient is 3.7602—indicating a level of future health risk almost four times that of the average member.

Example 3 includes a 52 year old female with two DCCs. The first DCC, riluzole, maps to the PRG for agents used in the treatment of ALS. The second DCC describes an antidepressant. The risk weights assigned to these PRGs, along with the age-sex weight for the member, produce an overall risk score of 13.145, more than 13 times that of the average member.

Therefore, while there has been described what is presently considered to be the preferred embodiment, it will understood by those skilled in the art that other modifications can be made within the spirit of the invention.

We claim:

1. A computer-implemented method for assessing risk of insuring a healthcare patient, the method comprising one or more computers performing the steps of:
   statistically determining a numerical risk weight for a plurality of risk groups using a large patient population; wherein, the large patient population has greater than 500,000 members;
   receiving demographic data for a patient and prescription data for a plurality of prescriptions filled by the patient;
   assigning the prescription data for at least one of the plurality of prescriptions that have an impact on a risk score to at least one of the plurality of risk groups based upon at least one medical condition typically treated by each prescription;
   not assigning the prescription data for at least one other of the plurality of prescriptions that have no impact on the risk score to any of the plurality of risk groups;
   calculating the risk score for the patient using risk data and the demographic data, the risk data including the risk groups for all prescription data of the patient and the numerical risk weight assigned to the plurality of risk groups; and
   in view of at least the risk score, at least one of adjusting payment rates, comparing provider performance, identifying patients of higher risk, or adjusting resources for differences in the risk score.

2. The method of claim 1, wherein the step of assigning the prescription data to at least one of the plurality of risk groups comprises using national drug codes to classify each of the plurality of prescriptions.

3. The method of claim 2, wherein the step of assigning the prescription data to at least one risk of the plurality of risk groups further comprises categorizing each national drug code classification into one of a number of pharmacy risk groups.

4. The method of claim 3, wherein the pharmacy risk groups comprise patient risk markers.

5. The method of claim 1, further comprising the step of defining additional patient risk groups based on patient age and co-morbidities known to indicate that the patient belongs to a high risk category and using the additional patient risk groups to calculate the patient's risk score.

6. The method of claim 1, further comprising the step of providing a demographic risk profile for the patient using at least the patient's age and gender and using the patient's demographic risk profile to calculate the patient's risk score.

7. The method of claim 1, further comprising the step of providing multiple patient risk groups for patients with pharmacy services that indicate multiple medical conditions and using the multiple patient risk groups to calculate the patient's risk score.

8. The method of claim 1, wherein the numerical risk weight is based upon the patient's demographic data, and the patient's risk score is the sum of the numerical risk weights of the plurality of risk groups in the patient's risk data.

9. The method of claim 8, wherein the risk score is computed using numerical risk weights and a patient's patient risk marker profile.

10. An information processing system comprising:
a computer processor for:
determining a numerical risk weight for a plurality of risk groups using multiple linear regression on a large patient population; wherein, the large patient population has greater than 500,000 members;
receiving demographic data for a patient and prescription data for a plurality of prescriptions filled by the patient;
assigning the prescription data for at least one of the plurality of the prescriptions that have an impact on a risk score to at least one of the plurality of risk groups using at least one medical condition typically treated by each prescription;
not assigning the prescription data for at least one other of the plurality of prescription that have no impact on the risk score to any of the plurality of risk groups;
calculating the risk score for the patient using risk data and the demographic data, the risk data including the risk groups for all prescription data of the patient and the numerical risk weight assigned to the plurality of risk groups; and
in view of at least the risk score, at least one of adjusting payment rates, comparing provider performance, identifying patients of higher risk, or adjusting resources for differences in the risk score.

11. A computer-implemented method for assessing risk of insuring a healthcare patient; the method comprising one or more computers performing the following:
determining a numerical risk weight for a plurality of risk groups using multiple linear regression on a large patient population; wherein, the large patient population has greater than 500,000 members;
receiving demographic data for a patient and prescription data for a plurality of prescriptions filled by the patient;
assigning the prescription data for at least one of the plurality of prescriptions that have an impact on a risk score to at least one of the plurality of risk groups based upon at least one medical condition typically treated by each prescription;
not assigning the prescription data for at least one other of the plurality of prescriptions that have no impact of the risk score to any of the plurality of risk groups;
assigning a numerical risk weight using the patient's demographic data;
calculating the risk score for the patient using a sum of the numerical risk values for the plurality of risk groups assigned using the prescription data and the numerical risk values assigned using the patient's demographic data; and
in view of at least the risk score, at least one of adjusting payment rates, comparing provider performance, identifying patients of higher risk, or adjusting resources for differences in the risk score.

12. The method of claim 11, wherein the step of assigning the prescription data to at least one of the plurality of risk groups comprises using national drug codes to classify each of the plurality of prescriptions.

13. The method of claim 12, wherein the step of assigning the prescription data to at least one of the plurality of risk groups further comprises categorizing each national drug code classification into one of a number of pharmacy risk groups.

14. The method of claim 13, wherein the pharmacy risk groups comprise patient risk markers.

15. The method of claim 11, further comprising the step of defining additional patient risk groups based on patient age and co-morbidities known to indicate that the patient belongs to a high risk category and using the additional patient risk groups to calculate the patient's risk score.

16. The method of claim 11, further comprising the step of providing a demographic risk profile for the patient based on the patient's age and gender and using the patient's demographic risk profile to calculate the patient's risk score.

17. The method of claim 11, further comprising the step of providing multiple patient risk groups for patients with pharmacy services that indicate multiple medical conditions and using the multiple patient risk groups to calculate the patient's risk score.

18. The method of claim 11, wherein calculating the risk score further uses pre-determined weights and a patient's patient risk marker profile.

* * * * *